United States Patent [19]
Jones

[11] Patent Number: 5,257,955
[45] Date of Patent: Nov. 2, 1993

[54] FIGURINE FOR DISPLAYING HUMAN BABY TEETH AND HAIR

[76] Inventor: Deborah S. Jones, P.O. Box 154, Webster, N.C. 28788

[21] Appl. No.: 873,412

[22] Filed: Apr. 24, 1992

[51] Int. Cl.$^5$ .......................... A63H 3/36; A63H 3/44
[52] U.S. Cl. ...................................... 446/73; 446/385; 446/394; 446/395; 428/16
[58] Field of Search ............... 446/395, 391, 394, 372, 446/72, 73, 385, 268; 428/16, 542.4; 434/264, 296

[56] References Cited

U.S. PATENT DOCUMENTS

| | | | |
|---|---|---|---|
| 1,627,511 | 5/1927 | Hopf | 446/394 |
| 2,904,929 | 9/1959 | Weih | 446/395 |
| 4,231,181 | 11/1980 | Fabricant | 434/264 X |
| 4,464,440 | 8/1984 | Dotzman | 428/542.4 |
| 4,777,745 | 10/1988 | Rose | 428/542.4 X |

*Primary Examiner*—Mickey Yu
*Attorney, Agent, or Firm*—Carter and Schnedler

[57] ABSTRACT

A figurine in the form of a doll or a doll's head is provided for displaying human baby teeth. The head includes an open mouth having a groove in the lower portion thereof. The human baby teeth are received in the groove and are held in place by epoxy. In addition, a cavity may be provided on the top portion of the doll's head for receiving human baby hair.

13 Claims, 2 Drawing Sheets

FIGURINE FOR DISPLAYING HUMAN BABY TEETH AND HAIR

BACKGROUND OF THE INVENTION

This invention relates to apparatus for displaying and preserving items from early childhood. More particularly it relates to apparatus for displaying and preserving human baby teeth.

Parents of young children often like to keep their children's baby teeth, locks of hair, and other items, such as clothing, as a remembrance of early childhood. Quite often the baby teeth and/or the hair are placed in an envelope or a box which is easily lost and, if not lost, is very seldom if at all opened and viewed by the parents. In addition, the clothing which was worn by the young child is often stored also in a box and forgotten, perhaps in a basement where it might deteriorate or be simply thrown away.

Various containers have been provided in the past to store baby teeth. U.S. Pat. No. 5,050,729 issued to Karbowniczak shows a container in the form of a fancy envelope including a pocket specifically designed to store baby teeth. U.S. Pat. No. 4,923,058 issued to Dennison shows a container for storing and displaying baby teeth in the form of a hinged box having a plurality of pockets. U.S. Pat. No. 4,091,481 issued to Redman shows a tooth pillow including a tooth receiving pocket which may be used to exchange teeth for coins. U.S. Pat. No. Des. 278,097 issued to Akiyoshi shows a case for baby teeth. U.S. Pat. No. Des. 208,781 issued to Zarganis also shows a storage case for baby teeth. None of these patents overcome the problem set forth above.

OBJECTS OF THE INVENTION

It is therefore one object of this invention to provide an improved apparatus for storing and displaying baby teeth.

It is another object to provide an improved apparatus for storing and displaying baby teeth and baby hair.

It is another object to provide an improved apparatus for storing and displaying baby teeth, human hair, and baby clothing.

It is still another object of this invention to provide an apparatus for storing and displaying baby teeth which is visually appealing and which may be displayed within a room in the house so that it is constantly in view in the room.

SUMMARY OF THE INVENTION

In accordance with one form of this invention, there is provided an apparatus for displaying human baby teeth including a three dimensional figurine. At least a portion of the figurine is shaped in the form of a human head. The figurine includes an opening forming a cavity in the shape of a human mouth. A mechanism is provided for securing at least one human baby tooth in the cavity. At least a portion of the human baby tooth is visible from outside of the opening.

Preferably the mechanism for securing the tooth in the cavity includes a groove in the cavity which receives the tooth and further receives an adhesive such as epoxy.

It is also preferred that a pair of baby teeth are received in the groove and that the groove be located in the lower portion of the mouth near the opening.

In addition, it is preferred that the figurine include a second cavity on the top portion of the head for receiving baby hair, which cavity receives an adhesive such as epoxy to hold the baby hair in the second cavity.

Furthermore, while the figurine could be in the form of a head, it is preferred that the figurine be in the form of a full bodied doll so that the doll may be dressed in clothing that the child would wear approximately at the time that the baby tooth or teeth were lost.

The doll with the baby teeth clearly visible in the mouth and having the human hair extending from the top of the head and being dressed in the child's clothing may be conveniently displayed in a room in the house so that all of the items are clearly visible to a person in the room at all times.

BRIEF DESCRIPTION OF THE DRAWINGS

The subject matter which is regarded as the invention is set forth in the appended claims. The invention itself however together with other objects and advantages thereof shall be better understood in reference to the following description taken in conjunction with the accompanying drawings in which:

DESCRIPTION OF THE PREFERRED EMBODIMENTS

Figure 1:
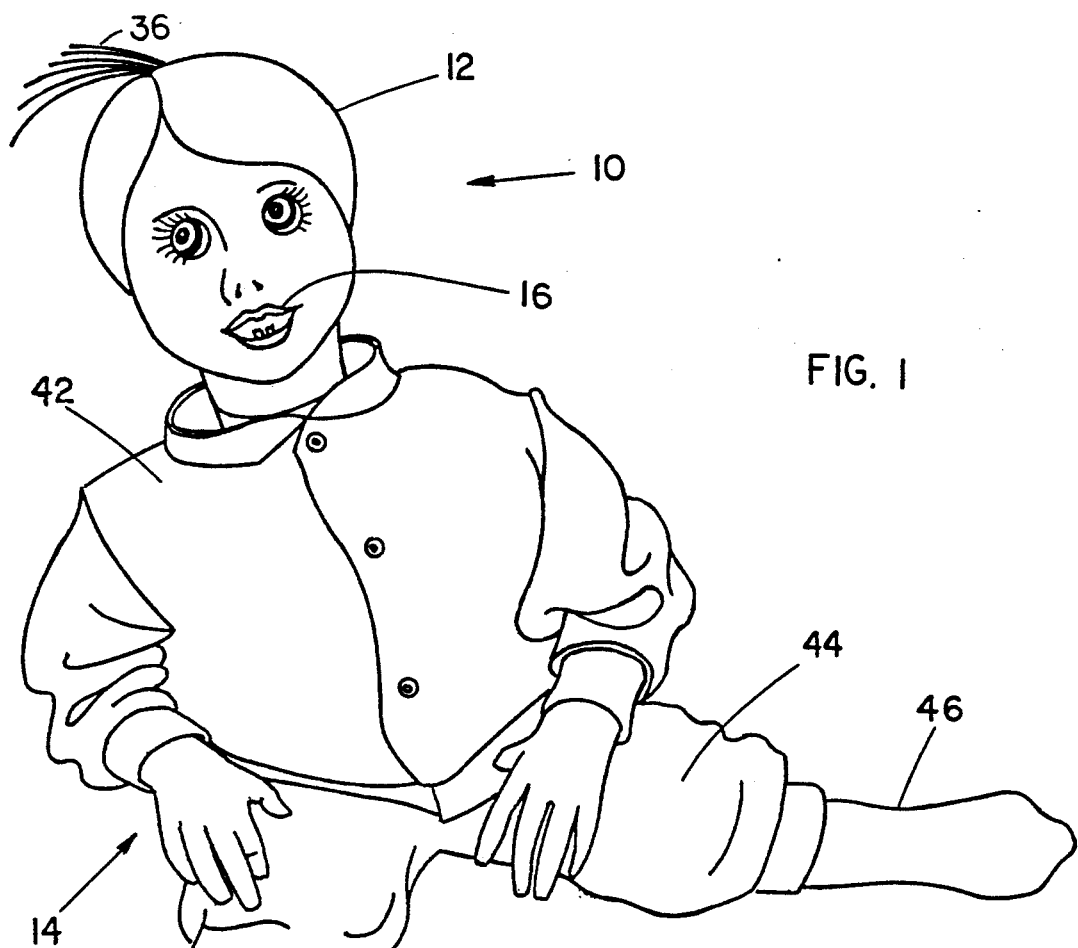
FIG. 1 is a pictorial view showing one embodiment of the invention.
Figure 2:
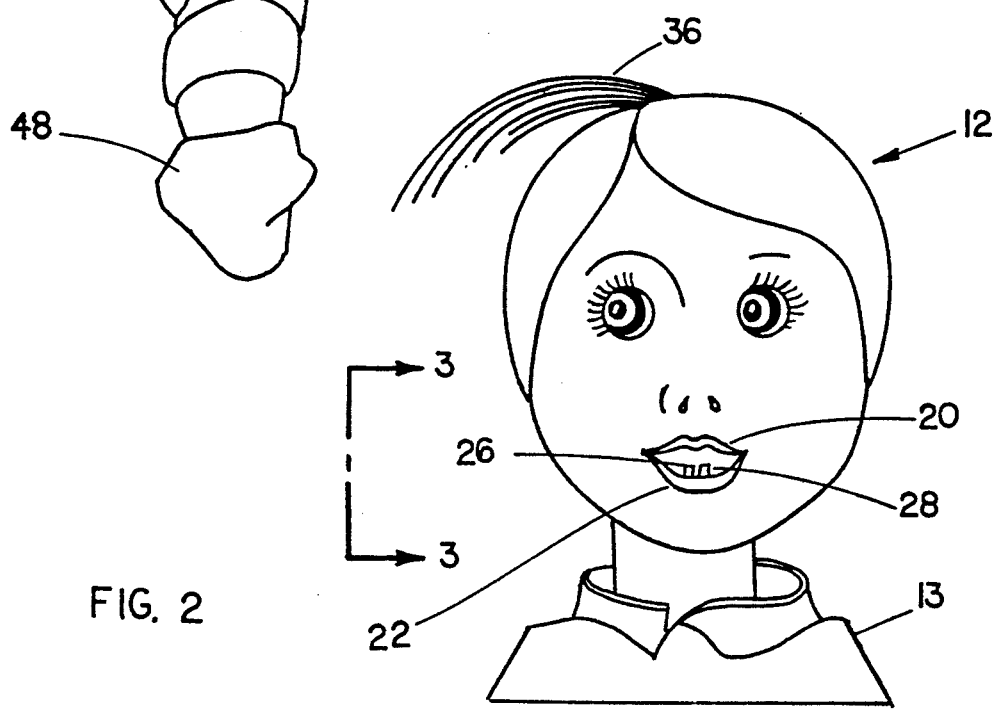
FIG. 2 is a front elevational view showing another embodiment of the subject invention which is essentially the head of the doll of FIG. 1 mounted on a platform.
Figure 3:
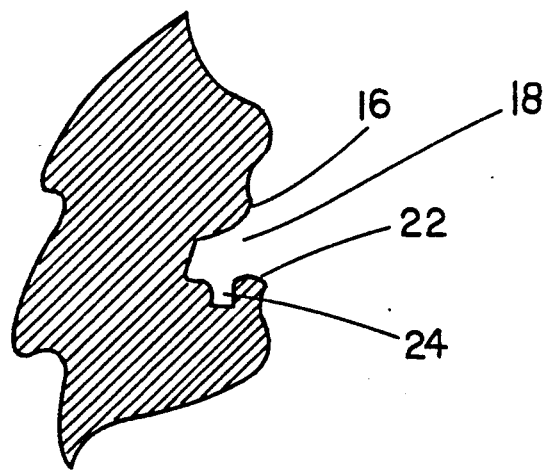
FIG. 3 is a sectional view of a portion of FIG. 2 taken through sectional lines 3—3.
Figure 4:
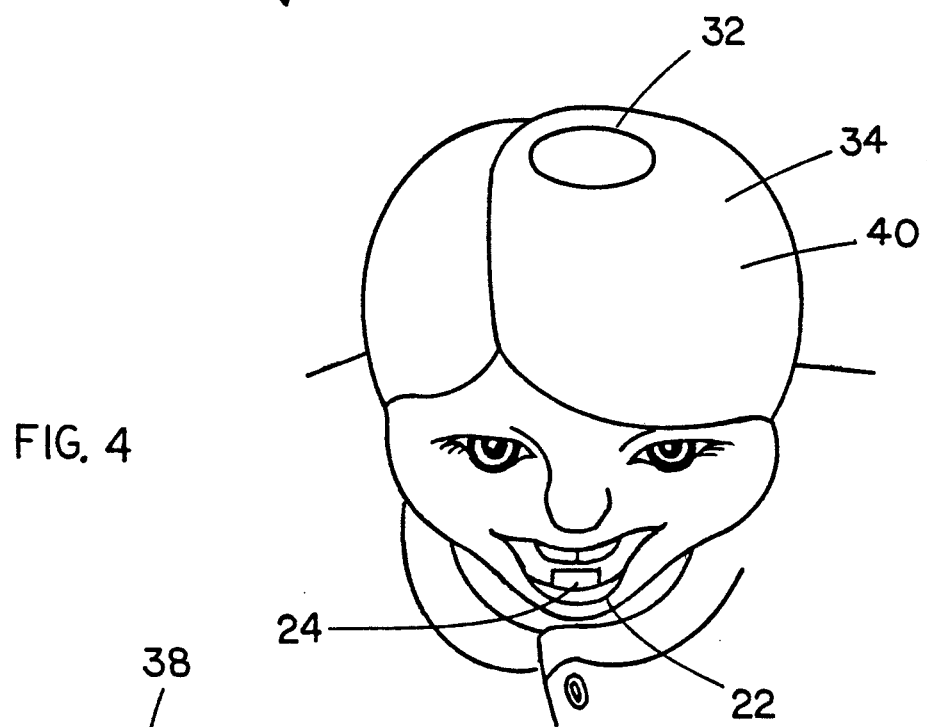
FIG. 4 is a pictorial view of the head portion of the apparatus of FIG. 1 with the head tilted forward and with the teeth and hair removed.
Figure 5:
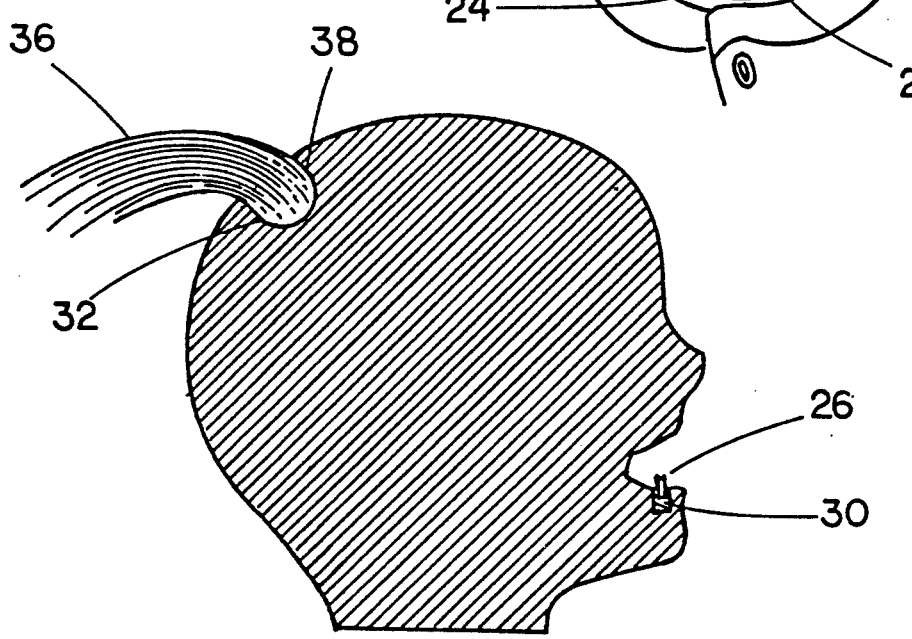
FIG. 5 is a sectional side elevational view of the apparatus of FIG. 2.

Referring now more particularly to FIGS. 1 through 5, there is provided a figurine which may be in the form of a doll 10 as shown in FIG. 1 or a doll head 12 mounted on platform 13 as shown in FIG. 2. Both the doll 10 and the doll head 12 are fully abled to be exhibited in an appealing manner in a room such as on a bookshelf.

Doll 10 as well as doll head 12 may be made of various materials but preferably are made of porcelain which is a material often used for keepsake type items. Doll 10 shown in FIG. 1 includes head 12 and body portion 14. So as to avoid confusion the head 12 on the doll 10 is numbered the same as the detached head 12 shown in FIG. 2.

Head 12 includes opening 16 forming a cavity 18. Opening 16 and the cavity 18 are in the form of an open human mouth. Upper and lower lips 20 and 22 are formed along the periphery of opening 16.

Elongated groove 24 is received in the lower portion of cavity 18 adjacent to lower lip 22. A pair of human baby teeth 26 and 28 are received in groove 24. Portions of the teeth extend above lip 22 so that those portions of the teeth are clearly visible from outside of opening 16. Groove 24 should be at least 3 millimeters deep so that the teeth are securely held in place but no more than 9 millimeters deep so that the teeth are clearly visible since the length of a typical lower middle baby tooth is between 10 and 15 millimeters. Preferably groove 24 is 6 millimeters deep.

The baby teeth 26 and 28 occupy the natural position of the middle lower baby teeth in the human body which are normally the first two baby teeth to fall out and thus are the two teeth that the parents will more than likely want to preserve.

An adhesive 30 such as epoxy is also received in groove 24 and contacts teeth 26 and 28 thereby firmly securing the teeth inside of cavity 18. Alternatively the teeth could be wedged into groove 24 if the groove is made so that an interference fit with the teeth is provided. This type of arrangement would work particularly well if the doll were made of a pliable material rather than porcelain. In that case the groove itself would serve to secure the teeth inside the cavity 18.

Preferably a second cavity 32 is provided in the top portion 34 of doll head 12. The second cavity receives the baby human hair 36 which is secured in cavity 32 by means of epoxy 38. One end of the cut hair may be held together by a rubber band (not shown) prior to placing it into cavity 32. The cavity is approximately one-half filled with epoxy. Also preferably the top of the head 34 is in the form of sculptured hair (nonfibrous) 40 so as to emphasize the human hair 36.

In the embodiment of FIG. 1 which shows the full doll 10, it is preferred that the body portion 14 of the doll be dressed with baby clothing such as shirt 42 and pants 44 and booties 46 and 48. It is preferred that the clothing in which doll is dressed is the clothing which the actual human baby wore at some time. Thus in the embodiment of FIG. 1, three very precious keepsake items are displayed on the doll, namely the baby's teeth, the baby's hair, and the baby's clothing. The doll may be displayed in a room so that it may be easily viewed by persons such as parents and grandparents. Thus not only are the teeth, the hair and the clothing preserved, they may be constantly on display in a convenient and aesthetically pleasing form which overcomes the problems of the prior art baby teeth containers, thereby generating memories and nostalgia associated with the early upbringing of one's child.

From the foregoing description of the preferred embodiments of the invention, it will be apparent that many modifications may be made therein. It is intended that the appended claims cover all such modifications which come within the true spirit and scope of the invention.

I claim:

1. An apparatus for displaying at least one human baby tooth comprising:
    a three dimensional figurine; at least a portion of said figurine shaped in the form of a human child's head; said figurine including an opening forming a cavity which is shaped in the form of a human mouth; at least one human baby tooth; a groove in said cavity; said groove being in the lower part of said cavity near said opening;
    said human baby tooth received in said groove; an adhesive material received in said groove and contacting said human baby tooth for securing said human baby tooth in said groove; at least portions of said human baby tooth being visible from the outside of said opening, whereby said human baby tooth is openly and permanently displayed in said figurine for facilitating reminiscence of early childhood.

2. An apparatus as set forth in claim 1 wherein said adhesive material is epoxy.

3. An apparatus as set forth in claim 1 wherein said at least one tooth includes a pair of teeth.

4. An apparatus as set forth in claim 1 further including upper and lower lips adjacent to the opening; said upper lip and said lower lip formed in the shape of human lips; said groove being adjacent to said lower lip; the depth of said groove being less than the length of human baby teeth.

5. An apparatus as set forth in claim 1 wherein said tooth is one of the middle lower teeth.

6. An apparatus as set forth in claim 1 wherein said figurine is in the form of substantially the entire body.

7. An apparatus as set forth in claim 6 wherein said figurine is dressed in a young child's clothing.

8. An apparatus as set forth in claim 1 further including a second opening forming a second cavity; said second cavity being in the top portion of the head; said second opening adapted to receive human hair.

9. An apparatus as set forth in claim 8 wherein said top portion of said head is sculptured in the shape of hair; said sculpture being nonfibrous whereby said human hair extending from said second cavity is emphasized.

10. An apparatus as set forth in claim 1 wherein said groove is between 3 millimeters and 9 millimeters deep.

11. An apparatus for displaying human baby teeth comprising:
    a three dimensional figurine in the form of a doll; a portion of said figurine shaped in the form of a human child's head; said head including an opening forming a first cavity in the shape of an open human mouth;
    upper and lower lips about the periphery of said first opening; said upper and lower lips shaped in the form of human lips;
    a groove received in said cavity adjacent to said lower lip;
    a pair of human baby teeth; said human baby teeth received in said groove;
    an adhesive material received in said groove and contacting said human baby teeth for securing said human baby teeth in said groove; at least portions of said human baby teeth being visible from the outside of said opening, whereby said human baby teeth may be openly and permanently displayed in said figurine for facilitating reminiscence of early childhood.

12. An apparatus as set forth in claim 11 further including a second cavity in said head near the top portion thereof; said second cavity receiving human hair; means for securing said human hair in said second cavity; portions of said human hair projecting out of said second cavity.

13. An apparatus as set forth in claim 11 further including a child's clothing received on portions of said doll.

* * * * *